United States Patent
Morales et al.

(10) Patent No.: US 11,356,608 B2
(45) Date of Patent: *Jun. 7, 2022

(54) SYSTEM AND METHOD TO OBTAIN A MOVING ENDOSCOPIC IMAGE

(71) Applicant: KARL STORZ Imaging, Inc., Goleta, CA (US)

(72) Inventors: Efrain Morales, Santa Ynez, CA (US); Marios Kyperountas, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/245,714

(22) Filed: Apr. 30, 2021

(65) Prior Publication Data
US 2021/0250506 A1    Aug. 12, 2021

Related U.S. Application Data

(63) Continuation of application No. 16/040,334, filed on Jul. 19, 2018, now Pat. No. 11,025,825.

(51) Int. Cl.
| | |
|---|---|
| H04N 5/217 | (2011.01) |
| A61B 1/04 | (2006.01) |
| H04N 5/232 | (2006.01) |
| A61B 1/00 | (2006.01) |
| A61B 1/05 | (2006.01) |
| G06T 7/00 | (2017.01) |

(52) U.S. Cl.
CPC ..... *H04N 5/23267* (2013.01); *A61B 1/00009* (2013.01); *A61B 1/05* (2013.01); *G06T 7/0012* (2013.01); *G06T 2207/10068* (2013.01); *G06T 2210/41* (2013.01); *H04N 5/23254* (2013.01)

(58) Field of Classification Search
CPC .. H04N 5/217; H04N 5/3532; H04N 5/23267; H04N 5/23254; A61B 1/00009; A61B 1/05; A61B 1/04; A61B 1/045; G06T 7/0012; G06T 2207/10068; G06T 2210/41

See application file for complete search history.

(56) References Cited

U.S. PATENT DOCUMENTS

| | | |
|---|---|---|
| 7,042,507 B2 | 5/2006 | Sato et al. |
| 7,298,401 B2 | 11/2007 | Baer |
| 8,310,530 B2 | 11/2012 | Bayer et al. |

(Continued)

OTHER PUBLICATIONS

Extended European Search Report, Application No. 19178813.2, dated Jan. 20, 2020.

*Primary Examiner* — Patrick E Demosky
(74) *Attorney, Agent, or Firm* — Michael Loi (57) ABSTRACT

A system and method includes operations and steps for obtaining a moving endoscopic image. An optical device stream is received from an optical device by data processing hardware. The data processing hardware identify image frames of the image stream, each including a plurality of rows of pixels. The data processing hardware determines a row exposure value for each of the rows of pixels in each frame, and identifies a defective image frame having at least one overexposed row and a reference frame having a replacement row corresponding to the overexposed row. The data processing hardware modifies the defective image frame by replacing the overexposed row with the corresponding replacement row of the reference frame.

20 Claims, 8 Drawing Sheets

(56) References Cited

U.S. PATENT DOCUMENTS

| | | |
|---|---|---|
| 8,803,962 B2 | 8/2014 | Modell et al. |
| 8,830,367 B1 | 9/2014 | Mobbs et al. |
| 9,265,408 B2 | 2/2016 | Modell et al. |
| 2006/0109373 A1 | 5/2006 | Kurane |
| 2008/0094482 A1 | 4/2008 | Yoshimura |
| 2008/0158396 A1 | 7/2008 | Fainstain et al. |
| 2009/0021588 A1* | 1/2009 | Border ............... H04N 5/23254 348/208.1 |
| 2009/0284637 A1* | 11/2009 | Parulski ........... H04N 5/232941 348/333.12 |
| 2009/0290033 A1 | 11/2009 | Jones et al. |
| 2011/0074943 A1 | 3/2011 | Modell et al. |
| 2014/0253704 A1* | 9/2014 | Modell ................. H04N 5/217 348/65 |
| 2015/0195487 A1 | 7/2015 | Liu et al. |
| 2015/0381890 A1* | 12/2015 | Povlick ................ G03B 15/05 348/241 |
| 2017/0123079 A1 | 5/2017 | Jacob et al. |

\* cited by examiner

SYSTEM AND METHOD TO OBTAIN A MOVING ENDOSCOPIC IMAGE

CROSS-REFERENCE TO RELATED APPLICATION

This application is a continuation of U.S. patent application Ser. No. 16/040,334, filed on Jul. 19, 2018, the contents of which are incorporated herein by reference.

TECHNICAL FIELD

This disclosure relates to obtaining a moving image for an endoscopic procedure.

BACKGROUND

Endoscopes are commonly used in the medical field for providing access to body cavities with decreased invasiveness. Rigid endoscopes include a rigid insertion tube, while flexible endoscopes typically include a flexible insertion tube. The insertion tubes, which extend from a hand piece or control portion, are configured to be inserted into a body cavity. A distal tip of the insertion tube includes an array of peripherals for providing various functions. For example, the distal tip may include lighting for illuminating the body cavity, one or more ports for delivering air or irrigation, suction ports for removing debris from the body cavity, a medical device or tool, and optics for providing a view of the body cavity to an operator of the endoscope.

Traditionally, the optics of the endoscope were provided mechanically, whereby lenses disposed in the distal tip of the insertion tube were in communication with an eyepiece on the hand piece of the endoscope via optical fiber cable or a series of rod lenses. However, modern endoscopes are often provided with electrical-based optics having one or more camera sensors disposed either at the distal tip of the insertion tube or on a proximal end of the insertion tube via a camera head that couples with a traditional optical endoscope. The camera sensors capture and deliver image signals to a camera control unit (CCU), which processes the image signals and outputs a video stream to a digital display.

Rolling shutter, complementary metal oxide semiconductor (CMOS) sensors are commonly employed in endoscopes due to their ability to provide reduced readout times and faster frame rates. The performance of rolling shutter CMOS systems can be affected by radiation pulses encountered during some endoscopic procedures. For example, during lithotripsy a medical device (e.g., a lithotripter) is used to provide pulses of focused, high-intensity shock waves (e.g., pressure waves) and/or electromagnetic radiation (e.g., laser) to break up stones that typically form in the kidney, bladder, ureters, or gallbladder. The pulses produced by the lithotripter may affect the imaging sensor in the imaging endoscope. For example, when electromagnetic radiation generated by the lithotripter is back-scattered to the imaging sensor, the radiation can temporarily overexpose many of the photo-sensitive elements (e.g., pixels) in the imaging sensor. Although the pulse is typically short in duration, any rows of a frame that are processed during the period of overexposure will consequently appear too bright on the display, a phenomenon known as banding. Accordingly, one or more frames of the video stream may have banding corresponding to rows of the frame that were affected by the radiation pulse.

Banding in the frame of a video stream can be adjusted by using known temporal filters, such as medial temporal filters or median temporal filters. However, temporal filters globally affect the frame, and often result in undesirable artifacts in the video stream, such as blurring or ghosting. Accordingly, there exists a need for modifying an endoscopic image stream to locally correct overexposure caused by radiation pulses.

SUMMARY

A system and method includes operations and steps for obtaining a moving endoscopic image. An optical device stream is received from an optical device by data processing hardware. The data processing hardware identifies image frames of the image stream, each including a plurality of rows of pixels. The data processing hardware determines a row exposure value for each of the rows of pixels in each frame, and identifies a defective image frame having at least one overexposed row and a reference frame having a replacement row corresponding to the overexposed row. The data processing hardware modifies the defective image frame by replacing the overexposed row with the corresponding replacement row of the reference frame.

One aspect of the disclosure provides a method. The method includes receiving, at data processing hardware, an image stream from an optical device. The data processing hardware then identifies image frames of the optical device stream, each of the image frames having an array of pixels including a plurality of rows. The data processing hardware determines a row exposure value for each of the rows in each of the image frames in the image stream, and then identifies a defective image frame including an overexposed row where differences among the row exposure values of neighboring rows of an image frame exceed a threshold value. In one embodiment of the method, the data processing hardware further identifies a reference image frame including a replacement row corresponding to the overexposed row of the defective image frame. The defective image frame is modified by the data processing hardware by replacing the overexposed row with the corresponding replacement row from the reference image frame of the optical device stream. In another embodiment, the data processing hardware applies a temporal filter median filter to the overexposed row of the defective image frame.

Implementations of the disclosure may include one or more of the following optional features. In some implementations, the method further includes generating a row-exposure curve for each image frame using the data processing hardware. Here, the difference between the row exposure values of the neighboring rows is provided as a slope of the row-exposure curve.

In some examples, the reference frame is at least one of the image frames immediately preceding and immediately succeeding the defective image frame.

In some implementations, the row exposure value is a sum of a pixel values for all pixels in a row.

In some implementations, the optical device is a rolling shutter complementary metal oxide semiconductor sensor.

In some examples, the method includes determining, by the data processing hardware, that the defective image frame should be modified where a modification threshold is satisfied.

In some implementations, the overexposed row of the defective image frame corresponds to a period of an electromagnetic radiation pulse.

Another aspect of the disclosure provides a system including data processing hardware and memory hardware. The memory hardware is in communication with the data processing hardware, and stores instructions that, when executed on the data processing hardware, cause the data processing hardware to perform operations. One of the operations may include receiving an optical device stream from an optical device. Another operation includes identifying image frames of the optical device stream, each of the image frames having an array of pixels including a plurality of rows. Additional operations can include determining a row exposure value for each of the rows in each of the image frames in the optical device stream, and then identifying a defective image frame including an overexposed row where a difference between the row exposure values of two neighboring rows of an image frame exceeds a threshold value. Another operation may include identifying a reference image frame including a replacement row corresponding to the overexposed row of the defective image frame. The defective image frame is modified by replacing the overexposed row with the corresponding replacement row from the reference image frame of the optical device stream.

This aspect may include one or more of the following optional features.

In some implementations, the method further includes generating a row-exposure curve for each image frame using the data processing hardware. Here, the difference between the row exposure values of the neighboring rows is provided as a slope of the row-exposure curve.

In some examples, the reference frame is at least one of the image frames immediately preceding and an immediately succeeding the defective image frame.

In some implementations, the row exposure value is a sum of the pixel values for all pixels in a row.

In some examples, the operations include applying a temporal filter median filter to the defective image frame.

In some implementations, the optical device is a rolling shutter complementary metal oxide semiconductor sensor.

In some examples, the method includes determining, by the data processing hardware, that the defective image frame should be modified where a modification threshold is satisfied.

In some implementations, the overexposed row of the defective image frame corresponds to a period of an electromagnetic radiation pulse.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
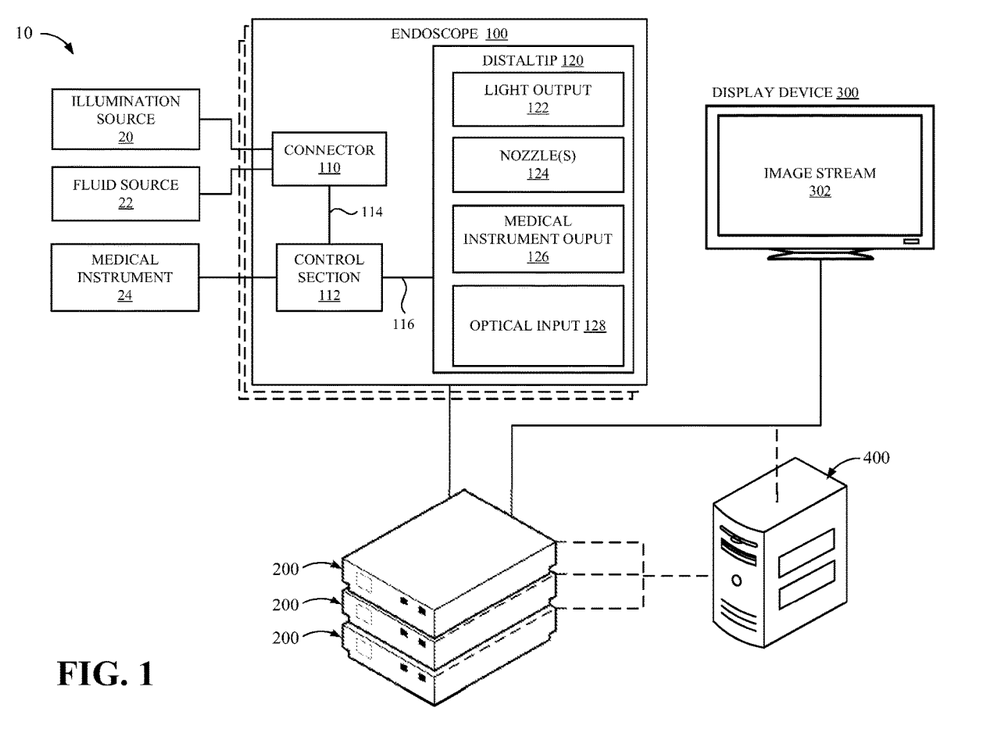
FIG. 1 is a schematic view of an example of a video endoscopic lithotripsy system.

Referring to FIG. 1 in some implementations, a video endoscopic lithotripsy system 10 includes an endoscope 100, a camera control unit (CCU) 200, and at least one display device 300. The system 10 may optionally include a camera control system 400 configured to function as a central interface between a plurality of camera control units 200 and a plurality of display devices 300. The endoscope 100 may be a rigid endoscope or a flexible endoscope, depending on the surgical procedure.

In one example of the system 10, a conventional endoscope 100 is provided. Generally, the endoscope 100 is configured to be inserted into a body cavity with decreased invasiveness. The endoscope 100 includes a connector 110 having one or more ports for connecting to input sources 20, 22. The endoscope 100 further includes a control section 112 connected to the connector 110 by a first flexible conduit 114, 114. The first flexible conduit 114 includes a plurality of conduits and fibers for delivering the various inputs (i.e. light, fluids) from the input sources 20, 22 to the control section 112. The control section 112 includes a plurality of valves for controlling a flow of the inputs therethrough. The control section 112 may further include a medical instrument port for receiving a medical instrument 24 of the system 10.

A second flexible conduit, referred to as an insertion tube 116, extends from the control section 112 to an articulable distal tip 120, and is configured to be inserted into the body cavity of the patient. Like the first flexible conduit 114, the insertion tube 116 includes a plurality of conduits and fibers for delivering the inputs and the medical instrument 24 between the control section 112 and the distal tip 120. In the illustrated example, the distal tip 120 includes a light output 122 for illuminating the body cavity, one or more nozzles 124 for fluid delivery and evacuation, a medical instrument output 126, and an optical input 128.

Although the endoscope 100 can be provided with a wide range of medical devices, such as forceps, brushes, or snares, the instant disclosure describes endoscopes 100 configured for lithotripsy procedures. Accordingly, the medical instrument 24 of the instant disclosure is an electromagnetic radiation emission device, such as a laser. The medical instrument 24 is configured to produce one or more pulses of electromagnetic radiation (e.g., laser radiation). The medical instrument 24 can be associated with multiple wavelengths (e.g., optical wavelengths), multiple power levels, and/or multiple pulse frequencies. In some embodiments, the pulses of electromagnetic radiation and/or synchronization pulses associated with the medical instrument output 126 can be generated by an electromagnetic radiation emission source (e.g., a laser source) coupled to the distal tip 120 of the endoscope 100 via an optical fiber (not shown), for example. Alternatively, the medical instrument 24 may be provided to the body cavity independently of the endoscope 100. In some examples, the electromagnetic radiation emission device is disposed outside of the body cavity, whereby the electromagnetic radiation is delivered to the body The optical input 128 is also disposed in the distal tip 120 and is configured to provide an image of the body cavity to the endoscope operator, thereby allowing the endoscope operator to locate the treatment area and monitor the medical procedure. Although mechanical optics (i.e. lenses) may be used, the instant disclosure is directed towards endoscopes having electrical optics, such as imaging sensors, which are in communication with an image processor to provide a digital display of the treatment area. The optical input 128 can be a complementary metal-oxide-semiconductor (CMOS) image sensor, a charge-coupled-device (CCD) image sensor, an infrared (IR) image sensor, a micro-electromechanical (MEM) array, or a focal plane array, for example. In one embodiment, the optical input 128 is configured to receive electromagnetic radiation in the visible range (e.g., between about 400 nm and 800 nm) and/or near infrared range (e.g., between about 800 nm and 1200 nm) associated with a particular field of view (e.g., area of treatment). As described in greater detail below, the optical input 140 delivers sensor data to a camera control unit 200, which processes the sensor data and outputs an image stream 302 to one or more display devices 300.

Figure 2A:
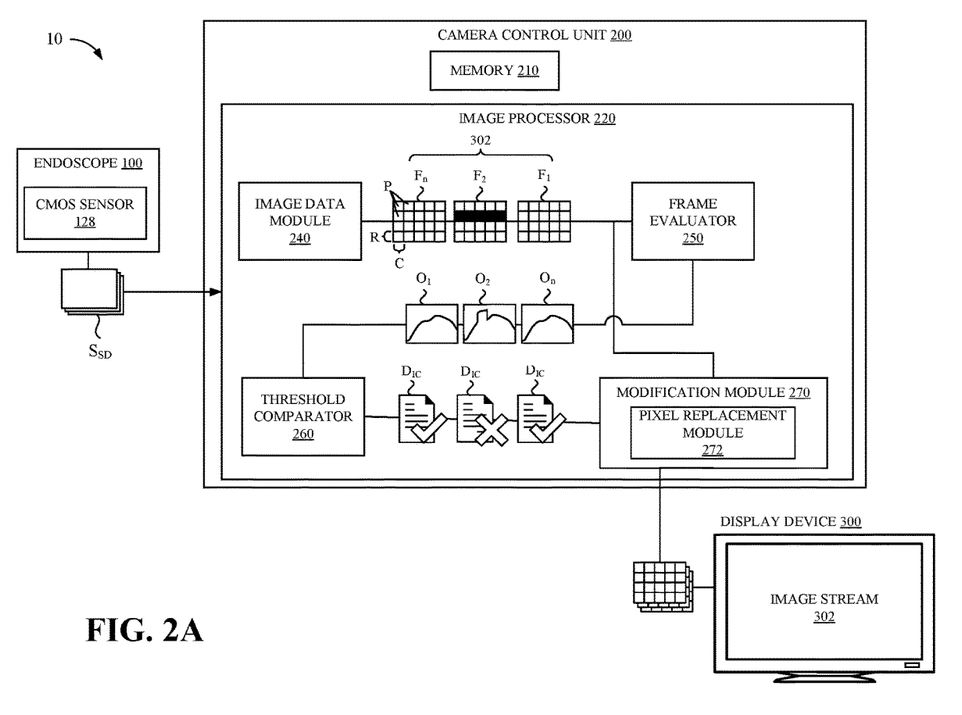
FIGS. 2A and 2B are schematic views of an example of a video endoscopic lithotripsy system.
Figure 2B:
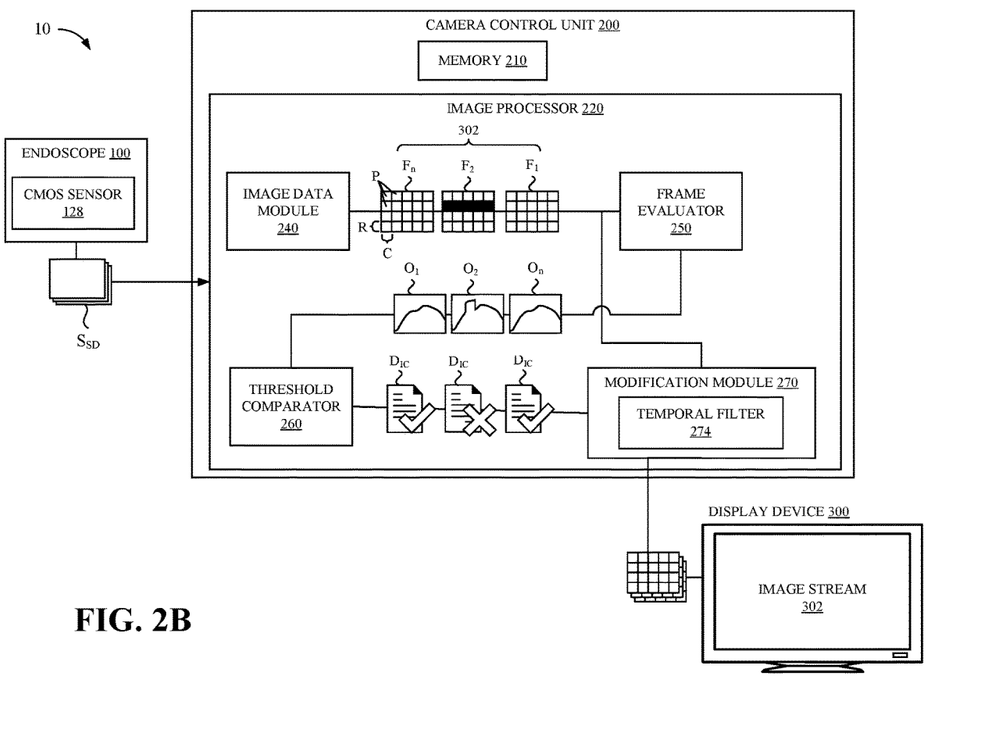

FIGS. 2A and 2B illustrate example operations of the camera control unit 200 of the system 10. The camera control unit 200 includes non-transitory memory 210 and an image processor 220. In some examples, the camera control unit 200 is configured as a local device, whereby each endoscope 100 is provided with a dedicated camera control unit 200. However, in some examples, the camera control unit 200 could be configured to operate on a server having data processing hardware and memory hardware, whereby a plurality of endoscopes 100 are managed by a single camera control unit 200.

The non-transitory memory 210 of the camera control unit 200 may include physical devices used to store programs (e.g., sequences of instructions) or data (e.g., program state information) on a temporary or permanent basis for use by a computing device. The non-transitory memory 210 may be volatile and/or non-volatile addressable semiconductor memory. Examples of non-volatile memory include, but are not limited to, flash memory and read-only memory (ROM), programmable read-only memory (PROM), erasable programmable read-only memory (EPROM), and electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Referring still to FIGS. 2A and 2B, the camera control unit 200 includes an image data module 240 for converting a sensor data signal $S_{SD}$ into an image stream 302, a frame evaluator 250 for determining image characteristics of each of the frames F of the image stream 302, a threshold comparator 260 for evaluating the image characteristics of each image frame F, and a modification module 270 for modifying image frames F that are flagged by the threshold comparator 260 as being unacceptable.

One or more of the components 240, 250, 260, 270 of the camera control unit can be software-based (e.g., set of instructions executable at a processor, software code) and/or hardware-based (e.g., circuit system, processor, application-specific integrated circuit (ASIC), field programmable gate array (FPGA)). Software (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The image data module 240 is configured to receive and process a sensor data signal $S_{SD}$ from the optical input 128 of the endoscope 100. In the illustrated example, the optical input 128 is a rolling shutter CMOS sensor 128. As is known in the art, the CMOS sensor 128 includes a pixel sensor array having a plurality of pixel sensors arranged in rows and columns. The pixel sensor array functions by converting light photons into electronic charges corresponding to each pixel, which are then delivered to the image data module 240 and processed to generate the viewable image frames F of the image stream 302, as described in greater detail below.

The frame evaluator 250 can be configured to receive the image frames F from the image data module 240 to determine image characteristics of each of the frames F. For example, the frame evaluator 250 may evaluate exposure levels of each of the pixels P in a respective one of the image frames F by measuring the respective pixel values of the pixels P. Pixel values may correspond to an integer representing a brightness of a pixel (e.g. 0 through 255) in greyscale image frames, or may be provided as a vector of three numbers representing color component (e.g. red, green, blue components) intensities in a colored image). Any form of pixel values (e.g. 8-bit, 32-bit signed, 32-bit floating) known in the art may be used. In some examples, the frame evaluator 250 is configured to determine a row exposure value for each row in the image frame by summing the pixel values of each of the pixels P forming the respective row R. Once the image characteristics for each frame are evaluated, the frame evaluator 250 may provide an image characteristic output O including the image characteristic values for each frame F. For example, where row exposure values are determined by the frame evaluator 250, the image characteristic output O may include a row-exposure curve 1100 plotting the row number of each row in a respective frame F against its corresponding row exposure value. Examples of row-exposure curves 1100 are provided in FIGS. 5A and 5B, which are described in greater detail below.

The threshold comparator 260 is configured to evaluate the image characteristic output O generated by the frame evaluator 250 to identify individual frames F of the image stream 302 that are defective or unacceptable. For example, the threshold comparator 260 may receive the image characteristic output O from the frame evaluator 250, and identify unacceptable frames based on whether a predetermined threshold is satisfied. In some examples, as provided above, the image characteristic output O is a row-exposure curve 1100 representing the saturation levels of each of the rows R in a given frame F.

As shown in FIGS. 2A and 2B, the modification module 270 is in communication with each of the image data module 240 and the threshold comparator 260, and is configured to modify one or more of the frames F of the image stream 302 based on the determination of the threshold comparator 260. For example, where the threshold comparator 260 determines that the image characteristic value associated with one of the frames F exceeds the predetermined threshold, the threshold comparator 260 will identify the frame as being defective, and will communicate the image characteristic data $D_{IC}$ to the modification module 270. The modification modules 270 then evaluates the image characteristic data $D_{IC}$ provided by the threshold comparator 260, and determines whether and how to modify a particular frame F.

Figure 3:
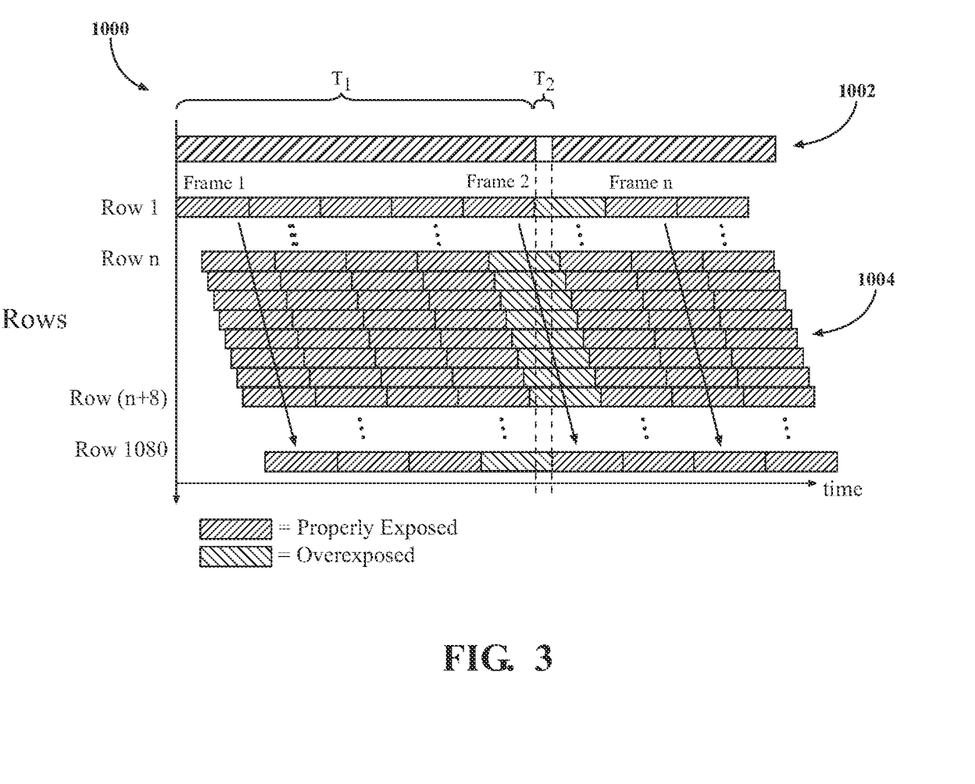
FIG. 3 is a diagram showing exposure overlap in a rolling shutter CMOS sensor.

With reference to FIGS. 2-5B, an example of a method for providing a modified video device stream using the camera control unit 200 is provided. As provided, a CMOS sensor 128 is provided at the distal tip 120 of the endoscope 100. In the operation of the CMOS sensor 128, rows of the pixel array of the CMOS sensor 128 are successively processed to generate the frames F of the image stream 302. As shown in FIG. 3, in a rolling shutter mode the sensor data $S_{SD}$ for each row of the pixel array is progressively processed to generate a frame F. Once a respective row of a first frame is exposed, the corresponding row of a subsequent frame begins processing.

During a lithotripsy procedure, pulses of electromagnetic radiation are delivered to a treatment area and may be reflected by the treatment area into one or more of the pixels of the sensor array. Consequently, rows of the pixel array being processed during the pulse of electromagnetic radiation may be subjected to higher levels of light than rows that are exposed before or after the radiation pulse, resulting in oversaturation of the respective rows.

With continued reference to FIG. 3, an example of the effect of electromagnetic radiation on frame exposure is provided. As shown, the chart 1000 provides an upper portion 1002 and a lower portion 1004. The upper portion illustrates periods of time T1, T3 where the lithotripter is not active and no electromagnetic radiation is emitted, which is represented as the hatched regions. As illustrated by the lower portion 1004 of the chart 1000, Frame 1 and Frame 3 are exposed or processed during the period where the lithotripter is inactive. Accordingly, none of the rows of Frames 1 and 3 are subjected to the radiation pulse, resulting in Frames 1 and 3 being free of any non-compliant or defective pixels.

Figure 4A:
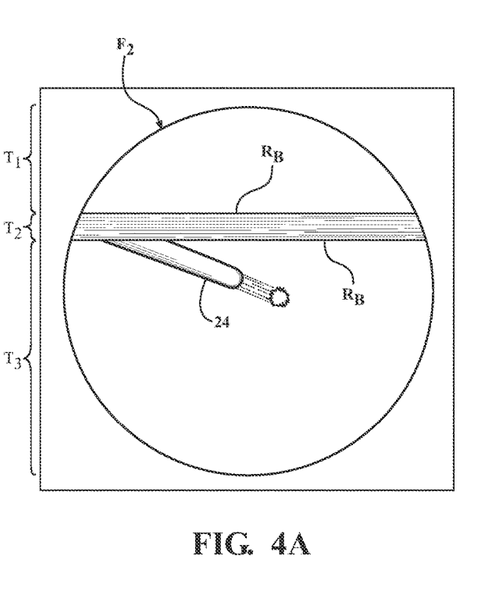
FIG. 4A is an example of a defective image frame having a plurality of defective rows.

Referring still to FIG. 3, the lithotripter is pulsed for a period of time T2 (i.e. unhatched region of upper portion 1002), whereby electromagnetic radiation is delivered to the treatment area of the body cavity. As shown, the illustrated rows of Frame 2 are exposed or processed during the period T2 where the lithotripter is actively emitting the radiation pulse. Here, the rows that are processed during the period T2 may be overexposed as a result of the temporarily elevated levels of radiation being absorbed by the CMOS sensor 128. As represented in FIG. 4A, frames F having rows R that are developed or processed during the radiation period T2 may appear as banded frames F, where the rows processed during the radiation period T2 have a relatively high pixel values compared to neighboring rows of Frame 2 that were processed or exposed outside of the radiation emission period T2.

When the sensor data signal $S_{SD}$ is processed by the image data module 240, the rows corresponding in time to the electromagnetic radiation pulse may appear as overexposed, such that the frames F of the image stream 302 including the overexposed rows appear banded. For example, as shown in FIG. 2, the first frame $F_1$ processed by the image data module 240 includes rows that were exposed prior to the radiation period T2, as indicated in FIG. 3. However, the second frame $F_2$ of the image stream 302 included rows R that were processed during the radiation period T2 and includes one or more rows R having an elevated exposure level, as illustrated by the solid black row in the second frame $F_2$ shown in FIG. 2 and shown in FIG. 4A. Subsequent frames $F_n$ in the image stream 302 will be provided without banding where the frames occur outside of the period T2 of the electromagnetic radiation pulse shown in FIG. 3.

Once the sensor data signal $S_{SD}$ is converted into the image stream 302, the frames F of the optical device stream are communicated to each of the frame evaluator 250 and the modification module 270. At the frame evaluator 250, image characteristics of each frame F are assessed to generate the image characteristic output O. In the illustrated example, the frame evaluator 250 is shown as receiving the processed frames F of the image stream 302 for evaluation. However, in some examples, the frame evaluator 250 may receive the sensor data signal $S_{SD}$ directly from the CMOS sensor 128, whereby the frame evaluator 250 independently determines the image characteristics for a given frame based on the preprocessed sensor data signal $S_{SD}$.

Figure 5A:
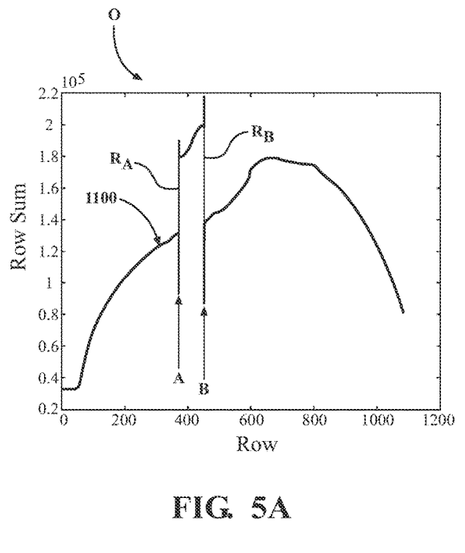
FIG. 5A is an example of a row-exposure curve corresponding to the defective image frame of FIG. 4A.
Figure 5B:
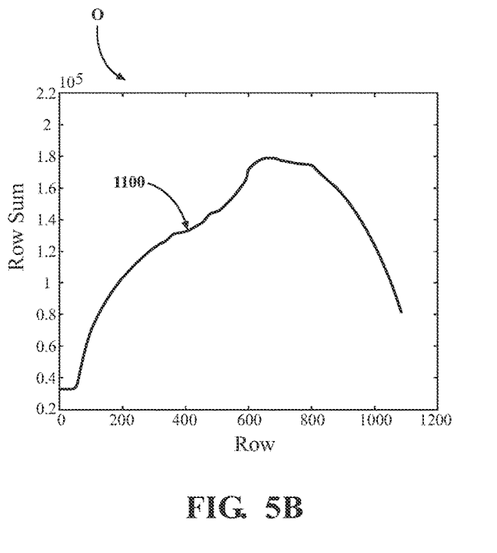
FIG. 5B is an example of a row-exposure curve corresponding to a reference image frame not having defective rows.

The frame evaluator 250 can be configured to assess image characteristics on a pixel-by-pixel basis, whereby each pixel P of each frame F is evaluated to determine the one or more image characteristics. For example, the frame evaluator 250 may determine a saturation level for each pixel P in a given frame F. The frame evaluator 250 then generates the image characteristic output O to be provided to the threshold comparator 260. In the illustrated example, the frame evaluator 250 is configured to determine a row exposure value for each row R in a given frame F by summing the exposure values for each pixel P of that row R. In some examples, the frame evaluator 250 may plot the row exposure values for each frame to generate a row-exposure curve 1100, as shown in FIGS. 5A and 5B. In some examples, the row-exposure curve 1100 is generated as a function of the row exposure value for every row in a frame, where the row exposure value for each row is plotted against the respective row number. For example, the illustrated row-exposure curve 1100 is based on a frame having 1080 rows along the x-axis, with the corresponding row exposure value of each row plotted against the y-axis. In some examples, such as when the image frames are processed using a filter, the row-exposure curve 1100 may be generated based on the row exposure values of neighboring rows that are commonly filtered. For example, where image frames are processed using a Bayer filter, the row-exposure curve 1100 may be generated based on semi-consecutive (i.e., every nth row) rows. That is a Bayer filter may have four filtering processes, commonly referenced as BGGR, RGBG, CRBG and RGGB wherein the rows are filtered sequentially by the filtering processes. In such case, the first row and the fifth row (both filtered by the BGGR filtering process) are compared. Here, the frame evaluator 250 may generate a first row-exposure curve for a first plurality of rows including alternatingly arranged green and red pixels, and a second row-exposure curve for a second plurality of rows including alternatingly-arranged green and blue pixels. In other examples, the row-exposure curve 1100 may be generated based on every third row or every fourth row of an image frame, where those rows are similarly filtered. Although the image characteristic output O of the illustrated example is shown graphically, the image characteristic output O may be a data-based output, whereby the raw image characteristic values are provided to the threshold comparator 260 for evaluation.

Referring again to FIG. 2, the threshold comparator 260 receives the image characteristic output O from the frame evaluator 250, and is configured to determine whether an individual frame F is acceptable as-is, or requires modification by the modification module 270. In the illustrated example, the threshold value is a threshold x-y slope value of the row-exposure curve 1100 generated by the frame evaluator 250, whereby the threshold comparator 260 will identify frames F as being defective when the row-exposure curve 1100 associated with the frame F has one or more sections that exceed the threshold x-y slope value. For example, as shown in FIG. 5A, the row-exposure curve 1100 includes an instantaneous increase in the row exposure values between neighboring rows at arrow A, and an instantaneous decrease in the row exposure values between neighboring rows of the row-exposure curve 1100 at arrow B. The instantaneous changes in row exposure values correspond to start and stop times for the radiation period T2, and result in the x-y slopes at each of the respective arrows being relatively high. For example, in the present example shown in FIG. 5, the threshold slope may be greater than approximately 7500 or roughly half of the jump shown at $R_A$. The threshold will depend upon the number of pixels in a row and the desired aggressiveness or responsiveness for detection of a defective row. Accordingly, the x-y slopes at the arrows will exceed the threshold x-y slope value and will be identified by the threshold comparator as being associated with defective rows R of a frame F.

In other examples, the frame evaluator 250 may store the row exposure value of preceding rows, current rows, and following rows in memory 210 to determine a rate of change or second order derivative of the row exposure curve. This second order derivative of the row-exposure curve for each row sum point may be monitored and compared against another threshold value by the threshold comparator 260 to assist with determination of whether or not to modify a given frame. Alternatively, a second order gradient may use three rows to determine whether or not to modify a frame. For example a current row sum may be doubled and a previous row sum and following row sum subtracted to determine a slope of a tangent line for the current row sum point on the row exposure curve. The slope or rate of change of the row sum may be compared with a threshold and/or hysteresis to determine when a defective row is present.

As shown in FIG. 2, the first arrow A identifies the beginning row $R_A$ of a group of rows that were exposed during the radiation period T2, while the second arrow B identifies the end row $R_B$ of the group of rows that were exposed during the radiation period T2. As shown in FIG. 4A, a distance between the beginning row $R_A$ and the end row $R_B$ correspond to a thickness of an oversaturated band of rows across the second frame F2. However, as discussed above, in some examples the row-exposure curve 1100 may be generated based on an image processed using a Bayer filter, whereby only every other row R of a frame F is included in the row-exposure curve. Thus, the neighboring rows of the row-exposure curve 1100 may not correspond to immediately adjacent rows R of the frame F, but instead may correspond to semi-consecutive rows R of the frame. In other examples, the row exposure curve 1100 may be generated based on other sequences or spacings of the rows R.

In yet other examples, more than one row exposure curve 1100 may be generated for an image based on different sequences or spacings of the rows R. Additionally or alternatively, the image characteristic output O may be based on the columns or individual pixels of each frame, as opposed to the rows. The threshold comparator 260 then provides image characteristic data $D_{IC}$ for each frame to the modification module 270, so that the modification module 270 may modify defective frames. The image characteristic data $D_{IC}$ may be as simple as identifying each frame as acceptable or unacceptable. In the illustrated example the image characteristic data $D_{IC}$ includes data related to the specific rows R of each frame F identified as being overexposed, such that the modification module 270 may modify only the rows, columns, or pixels identified as being overexposed, as opposed to replacing or removing an entire frame F.

Referring still to FIG. 2, the modification module 270 receives the raw image stream 302 from the image data module 240, including the defective frames F. The modification module 270 evaluates the image characteristic data $D_{IC}$ associated with each frame F and may determine if and how each frame F should be modified. For example, the threshold comparator 260 may provide image characteristic data $D_{IC}$ identifying a frame or series of frames as being defective, but the modification module 270 may make an independent decision as to whether the defect satisfies a predetermined modification threshold for repairing the frame. In some examples, the modification threshold may be a minimum number of rows, columns, or pixels P in a frame F that must be identified as being defective to warrant modification of the frame F. Additionally or alternatively, the modification threshold may be a minimum number of consecutive frames F that include defective rows to warrant modification of the frame F. For example, where a single frame has a single defective row R, the modification module 270 may ignore the defective frame F as being insignificant. On the other hand, where a significant number of consecutive frames F each include a significant number of defective rows, the modification module 270 will decide to modify one or more of the frames F.

If the modification module 270 determines that the modification threshold has been satisfied, the modification module 270 will identify one or more reference frames F for sampling, whereby the corresponding rows of the reference frame are identified by the threshold comparator 260 as being acceptable. For example, based on the image characteristic data $D_{IC}$ provided by the threshold comparator 260, the modification module 270 may identify the most immediately preceding or succeeding frames of the image stream 302 that includes acceptable rows corresponding to the defective rows of the defective frame F.

With reference to FIG. 2A, in one example of the system 10, the modification module 270 includes a pixel replacement module 272. The pixel replacement module 272 is configured to replace defective pixels, rows, or columns of the defective frames F with corresponding pixels, rows, or columns from the one or more reference frames identified by the modification module 270. In another example, shown in FIG. 2B, the modification module 270 includes a temporal filter 274 for applying one or more temporal filters (e.g., median temporal filter, mean temporal filter) to the defective pixels, rows, or columns of the defective frame. In some examples, the replacement module 272 is configured to incorporate a motion estimation step to decrease image artifacts that may arise from frame-to-frame misalignments due to local object motion. By utilizing localized modification methods according to the instant disclosure, only the defective rows of the defective frame F are replaced or filtered. This method minimizes undesirable artifacts (e.g. blurring, ghosting) that are found in known, global methods of frame modification, where entire frames are replaced or temporally filtered.

Figure 4B:
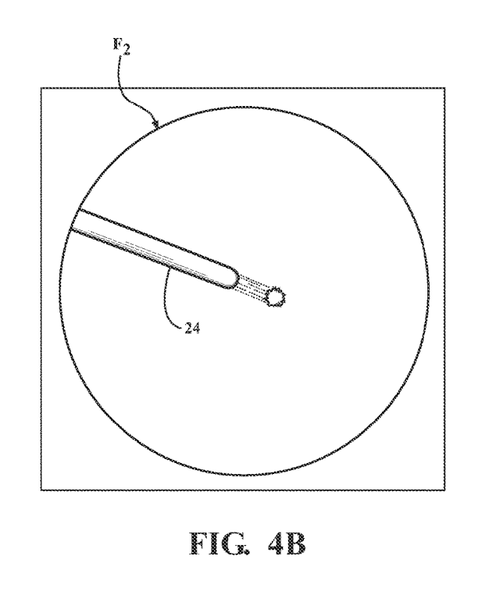
FIG. 4B is an example of a modified image frame, wherein the plurality of defective rows are replaced with corresponding replacement rows.

As shown in FIGS. 2A and 2B, the modified image stream 302 is then provided to the display device 300 by the camera control unit 200, whereby banding is removed from the frames F of the optical device stream. For example, FIGS. 4A and 4B illustrate an example of Frame 2, whereby FIG. 4A shows Frame 2 including a band of defective rows $R_A$-$R_B$, and FIG. 4B shows where the band of defective rows $R_A$-$R_B$ has been replaced from corresponding rows from the reference frame F.

The aforementioned system 10 is advantageous in that it efficiently identifies defective frames of a video stream without having to sample adjacent frames for reference. As explained above, each frame of the image stream 302 is evaluated independently to determine whether the frame includes defective pixels by relying on image characteristics of the particular frame. In one example, the row exposure values of each frame are plotted on the row-exposure curve, whereby a slope of the row-exposure curve is evaluated to determine whether rows of the frame are overexposed. In contrast, methods known in the prior art generally evaluate the image characteristics of a given frame against the image characteristics of adjacent frames to determine whether the frame is defective. By evaluating the frame locally, image latency is decreased and no additional digital memory within memory 210 is required. Image latency is the amount of time elapsed from the moment that an event occurs and its image is captured by a sensor 128 to the moment that the corresponding image stream 302 is displayed on a display device 300. If the frame were to be evaluated against the image characteristics of past adjacent frames, the past adjacent frames would be stored in additional digital memory within memory 210. If the frame were to be evaluated against the image characteristics of at least one future adjacent frames, the frame and zero or more future adjacent frames would be stored in additional digital memory within memory 210. Moreover, additional latency would be introduced because the image processor module would wait for the future adjacent frames to arrive from the endoscope 100.

Figure 6:
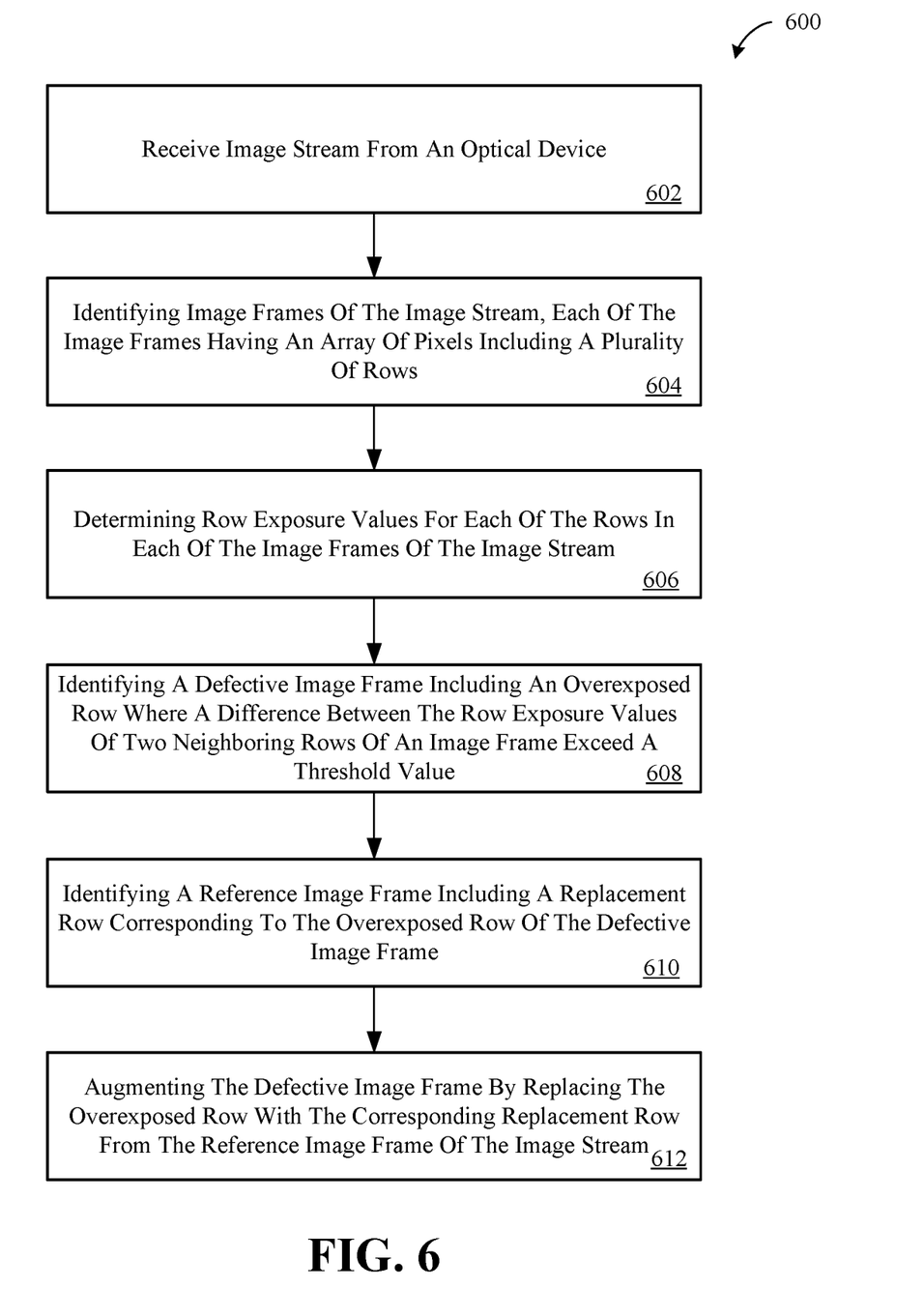
FIG. 6 is a flow diagram for an example method for identifying and correcting a defective image frame.

FIG. 6 illustrates a method 600 for modifying a frame of an optical device stream. At block 602, the method 600 includes receiving the image stream 302 from the optical input 128. At block 604, the method 600 includes identifying image frames of the optical device stream, each of the image frames having an array of pixels including a plurality of rows. At block 606, the method 600 includes determining row exposure values for each of the rows in each of the image frames of the optical device stream. At block 608, the method 600 includes identifying a defective image frame including an overexposed row where a difference between the row exposure values of neighboring rows of an image frame exceed a threshold value. At block 610, the method 600 includes identifying a reference image frame including a replacement row corresponding to the overexposed row of the defective image frame. At block 612, the method 600 includes modifying the defective image frame by replacing the overexposed row with the corresponding replacement row from the reference image frame of the image stream 302.

Figure 7:
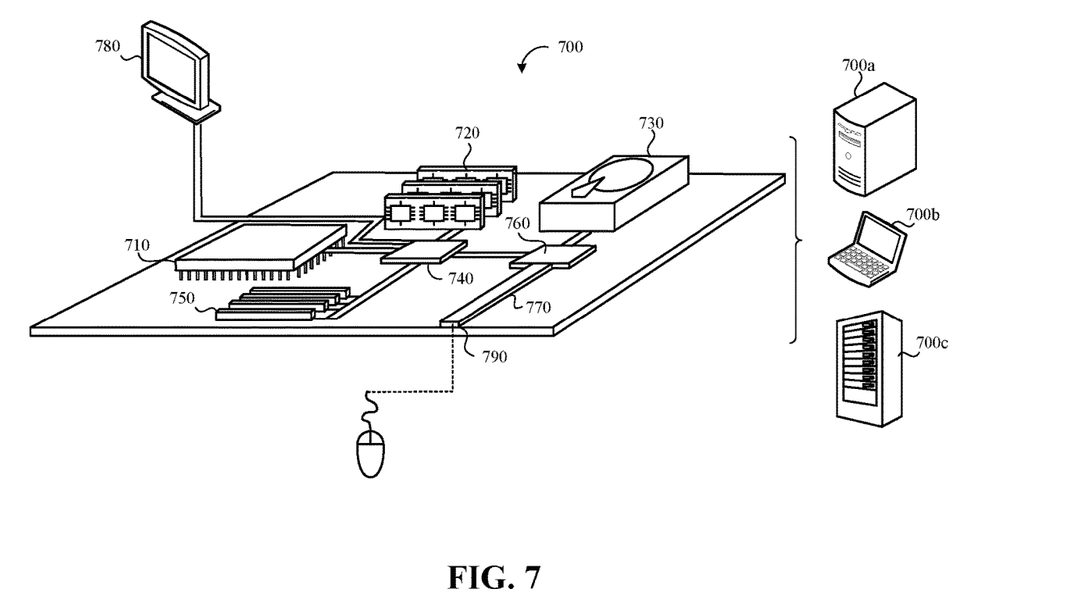
FIG. 7 is a schematic view of an example computing device that may be used to implement the systems and methods described herein.

FIG. 7 is schematic view of an example computing device 700 that may be used to implement the systems and methods described in this document. The computing device 700 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 700 includes a processor 710, memory 720, a storage device 730, a high-speed interface/controller 740 connecting to the memory 720 and high-speed expansion ports 750, and a low speed interface/controller 760 connecting to a low speed bus 770 and a storage device 730. Each of the components 710, 720, 730, 740, 750, and 760, are interconnected using various busses, and may be mounted on a common motherboard or in other manners as appropriate. The processor 710 can process instructions for execution within the computing device 700, including instructions stored in the memory 720 or on the storage device 730 to display graphical information for a graphical user interface (GUI) on an external input/output device, such as display 780 coupled to high speed interface 740. In other implementations, multiple processors and/or multiple buses may be used, as appropriate, along with multiple memories and types of memory. Also, multiple computing devices 700 may be connected, with each device providing portions of the necessary operations (e.g., as a server bank, a group of blade servers, or a multi-processor system).

The memory 720 stores information non-transitorily within the computing device 700. The memory 720 may be a computer-readable medium, a volatile memory unit(s), or non-volatile memory unit(s). The non-transitory memory 720 may be physical devices used to store programs (e.g., sequences of instructions) or data (e.g., program state information) on a temporary or permanent basis for use by the computing device 700. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 730 is capable of providing mass storage for the computing device 700. In some implementations, the storage device 730 is a computer-readable medium. In various different implementations, the storage device 730 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 720, the storage device 730, or memory on processor 710.

The high speed controller 740 manages bandwidth-intensive operations for the computing device 700, while the low speed controller 760 manages lower bandwidth-intensive operations. Such allocation of duties is exemplary only. In some implementations, the high-speed controller 740 is coupled to the memory 720, the display 780 (e.g., through a graphics processor or accelerator), and to the high-speed expansion ports 750, which may accept various expansion cards (not shown). In some implementations, the low-speed controller 760 is coupled to the storage device 730 and a low-speed expansion port 790. The low-speed expansion port 790, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 700a or multiple times in a group of such servers 700a, as a laptop computer 700b, or as part of a rack server system 700c.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims

What is claimed is:

1. A method comprising: receiving, at data processing hardware, an image stream from an imaging device; identifying, by the data processing hardware, image frames of the image stream, each of the image frames having an array of pixels including a plurality of rows; determining, by the data processing hardware, at least one row exposure value for each of the rows in each of the image frames in the image stream, the at least one row exposure value being a sum of the pixel values for all pixels in one of the rows; generating, by the data processing hardware, at least one row-exposure curve for each image frame based on the row exposure values for each of the rows in the image frame; identifying, by the data processing hardware, a defective image frame by identifying a defective row, the defective row being represented by an instantaneous change in a slope of the at least one row-exposure curve; identifying, by the data processing hardware, a replacement row from a reference image frame, the reference image frame being an image frame taken before the defective image frame, the replacement row being a row having a row-exposure curve spatially corresponding to the defective row; and modifying, by the data processing hardware, the defective image frame by replacing entirely the defective row with the replacement row.

2. The method of claim 1, wherein the reference frame is at least one of the image frames immediately preceding and/or immediately succeeding the defective image frame.

3. The method of claim 1, wherein the instantaneous change in the slope is an increase in the row exposure value which exceeds a threshold.

4. The method of claim 3, wherein the instantaneous change is a change which occurs within a predetermined number of adjacent rows.

5. The method of claim 1, wherein the row exposure value is a sum of the pixel values for all pixels in one of the rows.

6. The method of claim 1, further comprising applying, by the data processing hardware, a temporal filter median to the defective image frame.

7. The method of claim 1, wherein the optical device is a rolling shutter complementary metal oxide semiconductor sensor.

8. The method of claim 1, further comprising determining, by the data processing hardware, that the defective image frame should be modified where a modification threshold is satisfied.

9. The method of claim 8, wherein the modification threshold is at least one of a minimum number of defective rows of a defective image frame and a minimum number of consecutive defective image frames of the image stream.

10. The method of claim 1, wherein the overexposed row of the defective image frame corresponds to a period of an electromagnetic radiation pulse.

11. A video imaging system comprising: an endoscope; a light source coupled to the endoscope; a camera control unit; a display; wherein the camera control unit includes a data processing hardware, and a memory hardware in communication with the data processing hardware, the memory hardware storing instructions that when executed on the data processing hardware cause the data processing hardware to perform operations comprising: receiving, at data processing hardware, an image stream from an imaging device; identifying, by the data processing hardware, image frames of the image stream, each of the image frames having an array of pixels including a plurality of rows; determining, by the data processing hardware, at least one row exposure value for each of the rows in each of the image frames in the image stream, the at least one row exposure value being a sum of the pixel values for all pixels in one of the rows; generating, by the data processing hardware, at least one row-exposure curve for each image frame based on the row exposure values for each of the rows in the image frame; identifying, by the data processing hardware, a defective image frame by identifying a defective row, the defective row being a row having a pixel value exceeding a threshold value; identifying, by the data processing hardware, a replacement row from a reference image frame, the reference image frame being an image frame taken before the defective image frame, the reference image frame having a row-exposure curve spatially corresponding to the defective image frame, and wherein the replacement row is a row corresponding to the defective row; modifying, by the data processing hardware, the defective image frame by replacing the defective row with the replacement row so as to generate a corrected image frame; and displaying the corrected image frame on the display.

12. The video imaging system of claim 11, wherein the reference frame is at least one of the image frames immediately preceding and/or immediately succeeding the defective image frame.

13. The video imaging system of claim 11, wherein the defective image frame is a plurality of defective image frames, each of the plurality of the defective image frames are successive to each other.

14. The video imaging system of claim 11, wherein the row exposure value is a sum of pixel values for all pixels in one of the rows.

15. The video imaging system of claim 11, further including a temporal filter median to the defective image frame.

16. The video imaging system of claim 11, wherein the optical device is a rolling shutter complementary metal oxide semiconductor sensor.

17. The video imaging system of claim 11, wherein the data processing hardware includes a frame evaluator for generating the at least one row-exposure curve for each image frame and a threshold comparator for identifying the defective row.

18. The video imaging system of claim 11, further comprising determining that the defective image frame should be modified where a modification threshold is satisfied.

19. The video imaging system of claim 18, wherein the modification threshold is at least one of a minimum number of defective rows of a defective image frame and a minimum number of consecutive defective image frames of the image stream.

20. The video imaging system of claim 11, wherein the overexposed row of the defective image frame corresponds to a period of an electromagnetic radiation pulse.

* * * * *